Nov. 25, 1952 H. C. SWIM Plant Pat. 1,150
PEACH TREE
Filed Nov. 27, 1951
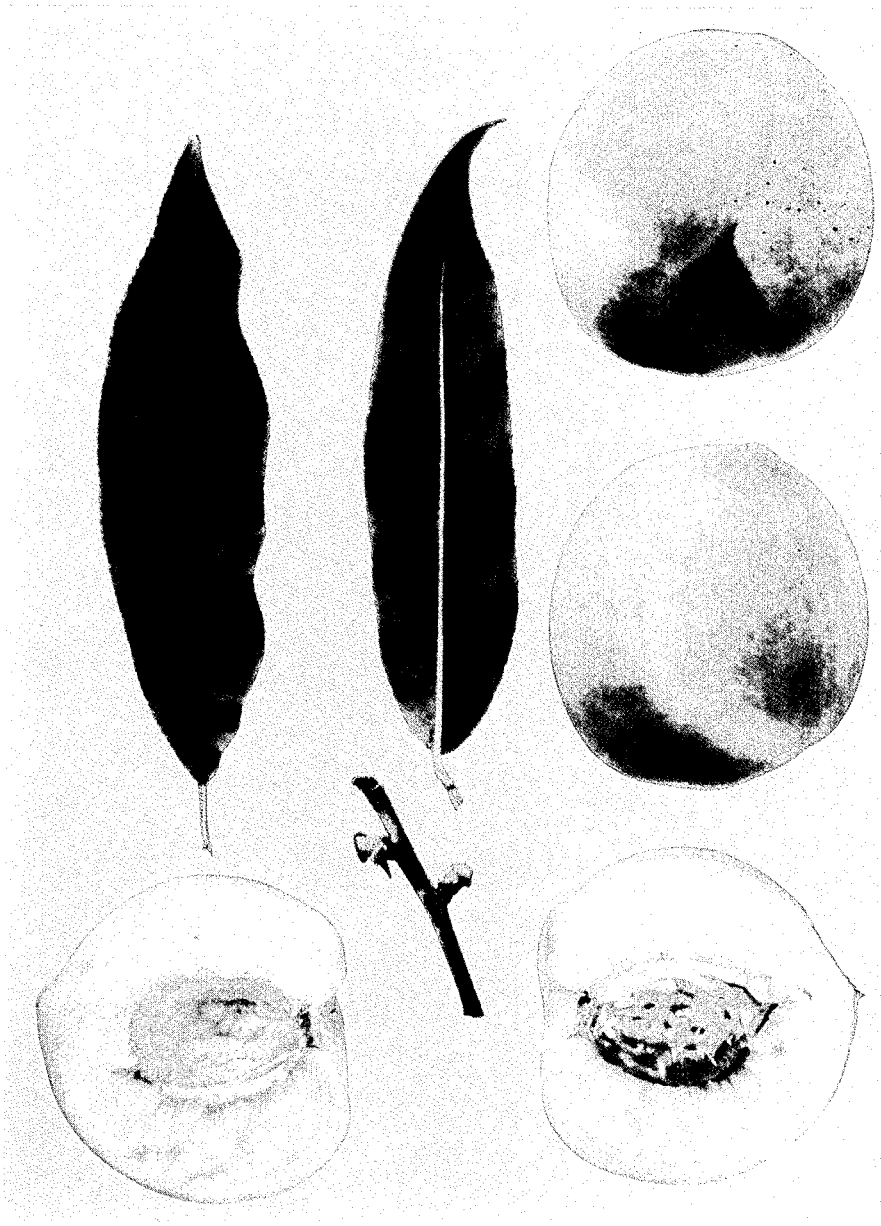
Inventor
H. C. Swim
By: Robert Robb
Attorneys Patented Nov. 25, 1952

Plant Pat. 1,150

UNITED STATES PATENT OFFICE 1,150

PEACH TREE

Herbert C. Swim, Ontario, Calif., assignor to Armstrong Nurseries, Inc., Ontario, Calif., a corporation of California Application November 27, 1951, Serial No. 258,318

1 Claim. (Cl. 47—62)

The present invention relates to a new and distinct variety of peach tree originated by me by crossing an unnamed and unpatented seedling of "Gold Mine" nectarine (unpatented) × "Rio Oso Gem" peach (Plant Patent No. 84) with an unnamed and unpatented seedling of "Gold Mine" nectarine × "July Elberta" peach Plant Patent No. 15.

The combination of yellow flesh and freestone fruit characteristics, with a shorter winter chilling requirement than any other peach of the same general type having a similar ripening period, establishes this new variety as distinctive and different from any other variety heretofore developed, and make the new variety especially suited to planting in southern California and similar areas where it has the ability to produce a fruit crop each year when winter temperatures are insufficient to satisfy the chilling requirements of standard varieties of similar type.

The fruit of the new variety is comparable in general appearance to that of "July Elberta," but usually ripens from 4 to 7 days earlier; the tree leafs out and flowers from 5 to 10 days earlier; has a shorter winter chilling requirement; and the fruit is slightly smaller in size, but has a sharper and superior flavor.

In comparison with "Rio Oso Gem," the new variety leafs out and flowers from 10 to 14 days earlier; has a shorter winter chilling requirement; the fruit ripens generally from 4 to 5 weeks earlier; and the fruit is somewhat more uniform in size and shape.

The aforementioned variety "Gold Mine" is a smooth-skin nectarine, while this new variety is definitely classed as a peach having down on the outer surface of the skin of its fruit.

The winter chilling requirement of this new variety is generally similar to that of the "Babcock" peach (unpatented), but this latter variety is a white-flesh, freestone peach, while my new variety is a yellow-flesh, freestone peach.

Asexual reproduction of my new variety by budding on seedling peach understock at Ontario, California, shows that the foregoing characteristics come true to form and are established and transmitted through succeeding propagations.

The accompanying drawing shows specimens of the fruit, foliage and a stem segment of my new variety, the fruit being shown in elevation and also in section both with and without the stone.

The following is a detailed description of the new variety, based upon observations of specimens grown at Ontario, California, with color terminology in accordance with Robert F. Wilson's Horticultural Colour Chart, except where Ridgway's Color Standards and Nomenclature are noted or where general color terms of ordinary dictionary significance are obvious:

Dates first and last picking—vary somewhat from year-to-year because of varying winter chilling in southern California, but usually begin picking about July 9th to July 16th, ending about July 17th to July 26th.

Tree: Medium size; medium vigor; open; vase-formed; very productive to productive; regular bearer.

*Trunk.*—Medium caliper in relation to length; medium surface roughness.

*Branches.*—Medium slender; mostly smooth; dull. Color—between Wood Brown, Plate XL (Ridgway), and Olive-Brown, Plate XL (Ridgway). Lenticels—numerous to medium number; medium size.

*Leaves.*—Size—large. Length, 5 inches to 6 inches. Width, 1⅛ inches to 1½ inches. Acuminate; lanceolate; medium thickness. Color: upper side of leaf—between Deep Dull Yellow-Green (1), Plate XXXII (Ridgway), and Dark Dull Yellow-Green, Plate XXXII (Ridgway); under side of leaf—between Chromium Green, Plate XXXII (Ridgeway), and Deep Dull Yellow-Green (1), Plate XXXII (Ridgway). Relatively smooth, wavy type. (As shown in article by Meader and Blake, "Progress report on identification of peach varieties by leaf characteristics," in American Society for Horticultural Science-Proceedings for 1939, volume 37, pages 203–207.) Margin—glandular; finely serrate. Petiole—medium in length; thick to medium in caliper. Glands—average number—usually 3, sometimes 4 to 5; opposite and alternate; medium size; globose and reniform, mixed; color—between Deep Sea-Foam Green, Plate XXXI (Ridgeway) and Chrysolite Green, Plate XXXI (Ridgway); Position—on margin of leaf just above petiole, and on petiole near attachment of leaf blade. Stipules—short; broad at base; early deciduous.

*Flower-buds.*—Large to medium size; long; conic; pointed; pubescent; bud scales with yellowish pubescence; free portion of calyx with greyish pubescence.

*Flowers.*—Dates first and full bloom—February 26th to March 11th; March 8th to 22nd.

Early compared with other varieties. Large; showy. Color—petal color of newly open flower—near Neyron Rose, Plate 623/2, page 76.

Fruit:

*Maturity when described.*—Eating ripe. Date—July 23.

*Size.*—Usually uniform; medium size. Diameter—axial, 2¼ to 2¾ inches; transverse in suture plane, 2½ to 2¾ inches; at right angles to suture plane, 2⅜ to 2⅝ inches.

*Form.*—Slightly variable; only slightly unsymmetrical; somewhat broadly ovoid; compressed laterally toward suture. Suture—generally shallow; extends from base to apex, but discontinuous at apex; has slight depression beyond pistil point. Ventril surface—slightly lipped toward apex on both sides, or sometimes not lipped at all; rarely lipped throughout; lips—unequal. Stem cavity—somewhat rounded; elongated in suture plane with suture showing on one side; depth, $\frac{3}{16}$ inch; breadth, $\frac{5}{16}$ inch. Base—rounded to occasionally slightly truncate. Apex—short; rounded to slightly truncate; pistil point—short; apical. Stem—length, $\frac{5}{16}$ inch; medium caliper; glabrous; adherence to stone—medium strength. Skin—medium to thin; medium texture; free; tendency to crack—none; color—varies from Aureolin, Plate 3/2, page 3, to Lemon Yellow, Plate 4/2, page 4; blushed with near Delft Rose, Plate o20/1, page 108, and near Claret Rose, Plate o21/1, page 109; down—moderate abundance; medium to short; does roll up when rubbed.

Flesh:

*Color.*—Lemon Yellow, Plate 4/2, page 4, to Buttercup Yellow, Plate 5/2, page 5; with small specks of Geranium Lake, Plate 20, page 20. Surface of pit cavity—somewhat marked (but not solidly marked) with Geranium Lake, Plate 20, page 20, to Carmine, Plate 21, page 21, and Buttercup Yellow, Plate 5/2, page 5; fibres also Buttercup Yellow, Plate 5/2, page 5.

*Amygdalin.*—Scant. Juice—abundant; rich.

*Texture.*—Medium firm; fine; melting.

*Fibres.*—Fine; tender.

*Ripens.*—Usually uneven; earliest at apex along lips.

*Flavor.*—Subacid; mild; good balance between sugar and acid.

*Aroma.*—Pronounced.

*Eating quality.*—Good.

Stone: Free; adheres to flesh along ventral edge.

*Fibres.*—Medium short; free on sides; retains some fibres in furrows.

*Size.*—Medium. Length, 1⅛ to 1⅜ inches. Breadth, ¾ to ⅞ inch. Thickness, ⅝ to ¾ inch.

*Form.*—Ovoid; cuneate toward apex.

*Base.*—Somewhat oblique. Hilum—narrow; oblong. Apex—acuminate.

*Sides.*—Only slightly unequal; curved on both sides. Surface—irregularly furrowed toward apex; ridged toward apex; pitted from base to above center; sometimes there are furrows and ridges near base.

*Ridges.*—Usually rounded toward base and apex.

*Pits.*—Elongated. Ventral edge—medium to thick, with wing generally throughout.

*Dorsal edge.*—Medium with shallow narrow groove toward base. Ridges on either side interrupted.

*Color of stone.*—Orange Cinnamon Plate XXIX (Ridgway), to Mikado Brown, Plate XXIX (Ridgway) with Scarlet-Red, Plate I (Ridgway) streaks along ventral edge and at base and apex.

*Tendency to split.*—None.

Use: Market; local; dessert.

Keeping quality: Medium.

Resistance to diseases: Good to medium for mildew.

Shipping quality: Medium.

I claim:

A new and distinct variety of peach tree of the yellow-flesh, freestone class, particularly characterized as to novelty by its relatively short winter chilling requirement comparable to that of the "Babcock" peach (unpatented), by its relatively early leafing, flowering and ripening habits, and by the relatively uniform shape, size and sharp, superior flavor of its fruit, substantially as shown and described herein.

HERBERT C. SWIM.

No references cited.